(12) United States Patent
Lokhat et al.

(10) Patent No.: US 9,073,883 B2
(45) Date of Patent: Jul. 7, 2015

(54) PRODUCTION OF HEXAFLUOROPROPYLENE OXIDE (71) Applicant: UNIVERSITY OF KWAZULU-NATAL, Westville (ZA)

(72) Inventors: David Lokhat, Durban (ZA); Maciej Starzak, Queensburgh (ZA); Deresh Ramjugernath, Durban (ZA)

(73) Assignee: UNIVERSITY OF KWAZULU-NATAL, Westville (ZA)

( * ) Notice: Subject to any disclaimer, the term of this patent is extended or adjusted under 35 U.S.C. 154(b) by 0 days.

(21) Appl. No.: 14/385,435

(22) PCT Filed: Mar. 15, 2013

(86) PCT No.: PCT/IB2013/052077
§ 371 (c)(1),
(2) Date: Sep. 15, 2014

(87) PCT Pub. No.: WO2013/136307
PCT Pub. Date: Sep. 19, 2013

(65) Prior Publication Data
US 2015/0073160 A1 Mar. 12, 2015

(30) Foreign Application Priority Data
Mar. 15, 2012 (ZA) .................. 2012/01951

(51) Int. Cl.
C07D 301/03 (2006.01)
C07D 301/08 (2006.01)
C07D 303/08 (2006.01)

(52) U.S. Cl.
CPC ............ *C07D 301/08* (2013.01); *C07D 303/08* (2013.01)

(58) Field of Classification Search
CPC ............................ C07D 301/08; C07D 303/08
USPC ........................................................ 549/523
See application file for complete search history.

(56) References Cited

PUBLICATIONS

International Search Report from Application No. PCT/IB2013/052077; filed Mar. 15, 2013.
"Expoxidation of Hexafluoropropylene"; by David Lokhat et al; Aiche Annual Meeting; dated Jan. 1, 2010.

*Primary Examiner* — T. Victor Oh
(74) *Attorney, Agent, or Firm* — Baker & Hostetler LLP (57) ABSTRACT A process for the production of HFPO includes introducing a feedstock comprising HFP and molecular oxygen into a heated reaction zone of a reactor. The reaction zone is at a reaction temperature $T_r$, where $180°$ C.$\leq T_r \leq 230°$ C. The feedstock is allowed to react, by epoxidation of the HFP, to produce HFPO. The HFPO is withdrawn from the reaction zone. The introduction of the feedstock into the reaction zone and the withdrawal of the product from the reaction zone is continuous.

8 Claims, 10 Drawing Sheets

PRODUCTION OF HEXAFLUOROPROPYLENE OXIDE

CROSS-REFERENCE TO RELATED APPLICATIONS

This application is a National Stage of International Patent Application No. PCT/IB2013/052077, filed Mar. 15, 2013, which claims priority to foreign South African Patent Application No. 2012/01951, filed Mar. 15, 2012, the contents of which are incorporated herein by reference in their entirety.

FIELD OF THE INVENTION

This invention relates to the production of 2,2,3-trifluoro-3-(trifluoromethyl)oxirane, commonly known as hexafluoropropylene oxide (HFPO), in particular the gas phase production of HFPO from hexafluoropropylene (HFP) and molecular oxygen.

BACKGROUND OF THE INVENTION

HFPO, the epoxide product of the partial oxidation of HFP, is a highly reactive and versatile intermediate that can be converted to perfluoroalkylvinylethers. It is used in the production of proton-exchange members for fuel cells and to make heat-resistant fluids, high-temperature lubricants, high-performance elastomers and surfactants. Known non-catalytic epoxidation processes for the production of HFPO suffer from various problems such as the production of large quantities of environmentally unfavourable waste and/or high reagent costs due to the use of solvents and/or chemical oxidising agents such as hypohalites, hydrogen peroxide and organic peroxides, which can also be hazardous to operators. Moreover, with known non-catalytic batch processes which employ oxygen as the oxidising agent for the epoxidation of HFP, it is difficult to achieve adequate rates of production of HFPO. This invention seeks to ameliorate the abovementioned problems, at least to some extent, while achieving an adequate rate of production of HFPO i.e. a good selectivity towards HFPO at an acceptable yield.

SUMMARY OF THE INVENTION

According to a first aspect of the invention, there is provided a process for the production of HFPO, which process includes:
  introducing a feedstock comprising HFP and molecular oxygen into a heated reaction zone of a reactor, with the reaction zone being at a reaction temperature $T_r$, where $180°\ C.\leq T_r \leq 230°\ C.$;
  allowing the feedstock to react, by epoxidation of the HFP, to produce HFPO; and
  withdrawing the HFPO from the reaction zone,
with the introduction of the feedstock into the reaction zone and the withdrawal of the product from the reaction zone being continuous.

The process may include pretreating the reactor by heating the reaction zone of the reactor to a pretreatment temperature $T_p$, where $180°\ C.\leq T_p \leq 230°\ C.$, and thereafter passing gaseous HFP and oxygen through the reaction zone at a first HFP:$O_2$ molar ratio, x, for a period of time, while maintaining the pretreatment temperature $T_p$ in the reaction zone; and thereafter adjusting the HFP:$O_2$ molar ratio to a second value, y, where $y \neq x$, to achieve the HFPO production.

The pretreatment temperature, $T_p$, is preferably approximately 200° C.

The process thus includes maintaining the reaction zone, during the conversion of HFP to HFPO after the pretreatment of the reactor, i.e. during a HFPO production phase, at the reaction temperature $(T_r)$ of 180° C. to 230° C. More preferably, Tr is 200° C.-215° C., still more preferably 205° C.-210° C., most preferably about 207° C.

The molar ratio, x, of HFP:$O_2$ may be about 1:1, while the molar ratio, y, of HFP:$O_2$ may be in the range of 0.25:1 to 1.81:1, provided that y is not the same as x. More preferably, the molar ratio, y, of HFP/$O_2$ is in the range of 1:1-1.4:1, still more preferably 1.1:1-1.35:1, most preferably about 1.2:1. It will be appreciated that y will be selected to enhance the conversion of HFP and the yield of HFPO, with the selection of y taking into account the reaction temperature, $T_r$, and the residence time (space time) of the feed (HFP and $O_2$) in the reaction zone.

The period of time that the reactor is pretreated may be at least 60 hours, and may be up to 80 hours.

The pressure in the reactor, during the pretreatment as well as subsequently, may be 3 to 6.5 bar, preferably about 4.5 bar. Such a moderate operating pressure is advantageous in that industrial experience has shown that the operational risk associated with processes using high pressures, even in the liquid phase, is generally greater. This may be explained in terms of the reaction mechanism. The oxidation of HFP is a complex free-radical chain process involving initiation, branching and termination steps. In a radical chain reaction scheme there exists competition for radicals or chain carriers between the branching and termination steps. If the propagation steps produce more chain carriers than the termination steps consume, the reaction can become self-accelerating. The population of the chain carriers grows exponentially and detonation occurs. For the HFP-$O_2$ system, this sequence of events is more likely to occur at higher pressures.

The gaseous residence or space time of the feedstock in the reaction zone during the pretreatment as well as subsequently, during the HFP conversion to HFPO, i.e. during the HFPO production phase, may be in the range of 80 to 160 seconds, e.g. about 120 seconds.

In the process, the HFP/$O_2$ feedstock is thus fed continuously into the reaction zone, while the HFPO product is withdrawn continuously from the reaction zone. The process is thus a continuous process.

The HFP/$O_2$ feed rate may be such that flow through the reaction zone is laminar.

The reactor may be in the form of a cylindrical tube of constant cross-sectional area and fabricated from metal. The metal preferably is, or includes, copper. The reactor tube is accordingly copper-based, and may thus be of copper. The reactor tube may have a surface-to-volume ratio of at least $2000\ m^{-1}$, preferably about $2670\ m^{-1}$. The reactor tube may be helically coiled. The reactor tube may be located in a jacket containing a heat transfer fluid, for example oil, the reactor tube being immersed in the heat transfer fluid. The interior of the jacket may be in flow communication with a heating apparatus for heating the oil to the pretreatment temperature $(T_p)$ and to the reaction temperature $(T_r)$ and maintaining it, so that the inside of the reactor tube, i.e. the reaction zone, will be maintained at the pretreatment temperature $(T_p)$ or the reaction temperature $(T_r)$.

Use of small diameter tubing and copper as material of construction results in efficient removal of reaction heat, e.g. since copper has both a relatively good thermal conductivity and a relatively high thermal mass. To a lesser extent, increased rates of heat transfer are obtained in the coiled tubes due to secondary flow (in the direction perpendicular to the axial flow) through the action of centrifugal force on fluid elements.

The pretreatment of the reactor may include a preparatory drying step for removing any moisture from the reactor prior to commencing passage of the HFP and the oxygen through the reactor. The preparatory drying step may include heating the reactor and/or passing a chemically inert gas, e.g. helium, through the reactor.

It is believed that the pretreatment step results in higher subsequent values of HFP conversion and of HFPO yield due to a gradual build-up of a film of high-molecular weight, oligomeric oxidation products on the inner surface of the reactor tube, which as indicated above may be of metal, and it is postulated that this results in passivation of the surface, which results in the higher conversion and yield values.

According to a second aspect of the invention, there is provided a process for the production of HFPO, which process includes:

introducing a feedstock comprising HFP and molecular oxygen into a heated reaction zone of a reactor comprising a copper-based cylindrical tube of constant cross-sectional area, with the tube being helically coiled and having a surface-to-volume ratio>2000 $m^{-1}$, with the reaction zone being at a reaction temperature $T_r$, where 180° C.$\leq T_r \leq$230° C.;

allowing the HFP and the molecular oxygen to react, by epoxidation of HFP, to produce HFPO; and withdrawing the HFPO from the reaction zone, such that there is laminar flow of the feedstock and the HFPO through the reaction zone.

According to a third aspect of the invention, there is provided a process for the production of HFPO, which includes pretreating a reactor by heating a reaction zone of the reactor to a pretreatment temperature $T_p$, where 180° C.$\leq T_p \leq$230° C., and thereafter passing gaseous HFP and oxygen through the reaction zone at a first HFP:$O_2$ molar ratio, x, for a period of time, while maintaining the pretreatment temperature $T_p$ in the reaction zone; and thereafter adjusting the HFP:$O_2$ molar ratio to a second value, y, where y$\neq$x, with the HFP being converted by means of epoxidation to HFPO.

As indicated in the introductory portion above, it is difficult to achieve adequate rates of production of HFPO with known batch processes. It has, however, unexpectedly been found that if there is careful temperature regulation, adequate yield of, and selectivity for, HFPO can in fact be achieved. It is believed that there is a propensity for the oxirane structure of HFPO to decompose at the elevated temperatures that are needed for initiation of the epoxidation reaction and that the problem is exacerbated because of high temperatures being obtained due to localised exothermic heat effects. It is believed that inefficient removal of reaction heat from conventional batch reactors has been a reason why they have been unable to achieve adequate rates of production of HFPO. It is further believed that a high reactor surface-to-volume ratio as well as heat transfer enhancement through the action of secondary flow in a coiled reactor tube also promotes HFPO yield by allowing for efficient removal of reaction heat.

Moreover, as hereinbefore set out, the reactor may be a cylindrical tube of constant cross-sectional area fabricated from metal, preferably copper. The use of copper is advantageous since it has both a relatively good thermal conductivity and a relatively high thermal mass, the combination of which is conducive to good temperature control. The reactor tube may have a surface-to-volume ratio of at least 2000 $m^{-1}$, preferably about 2670 $m^{-1}$. The continuous feedstock (HFP/$O_2$) flow rate into the reactor tube may be 100-200 ml/min, which provides laminar flow through the reactor tube. The reactor tube may be helically coiled.

The invention will now be described in more detail by way of non-limiting example and with reference to the accompanying schematic drawings.

DETAILED DESCRIPTION

Figure 1:
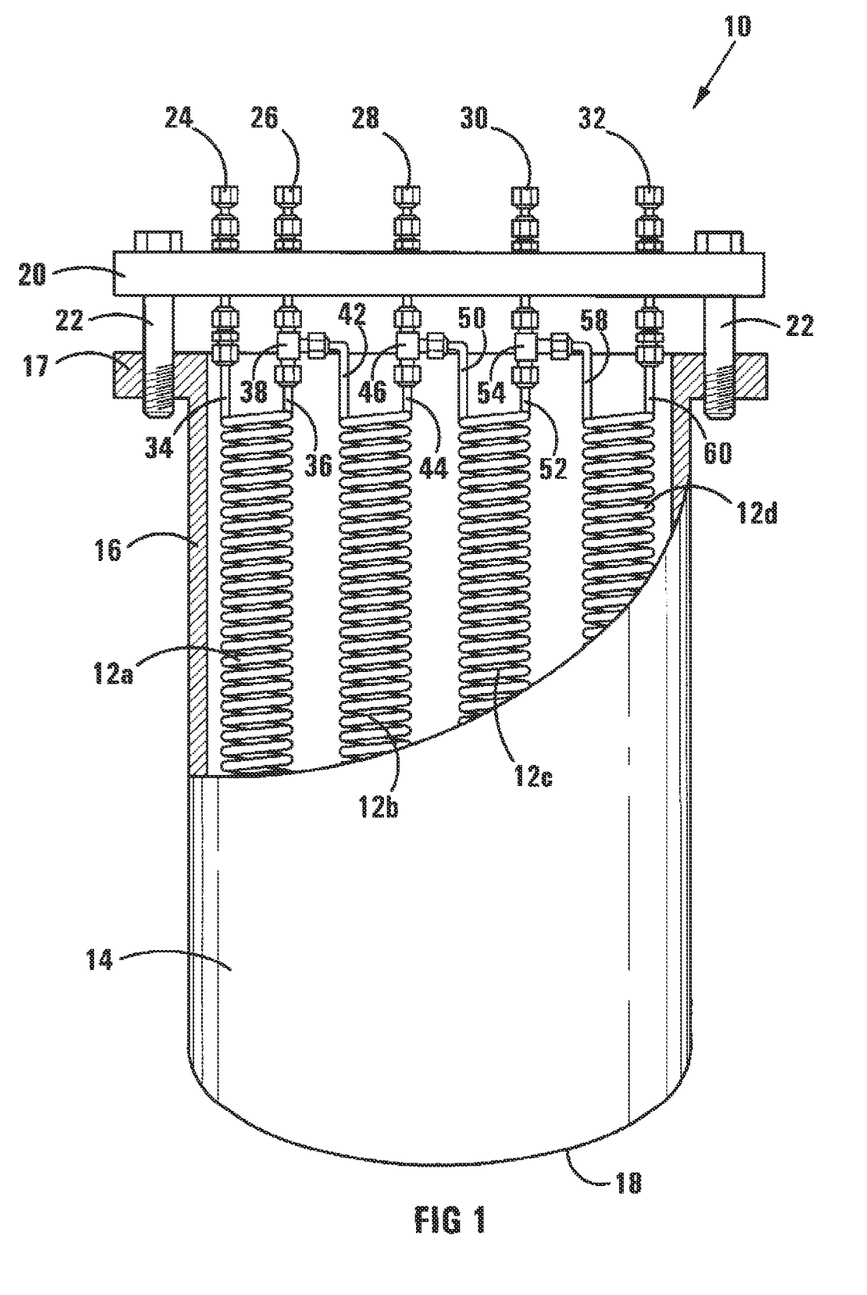
FIG. 1 shows a longitudinal partial sectional view of a reactor in which a process according to the invention may be carried out.
Figure 2:
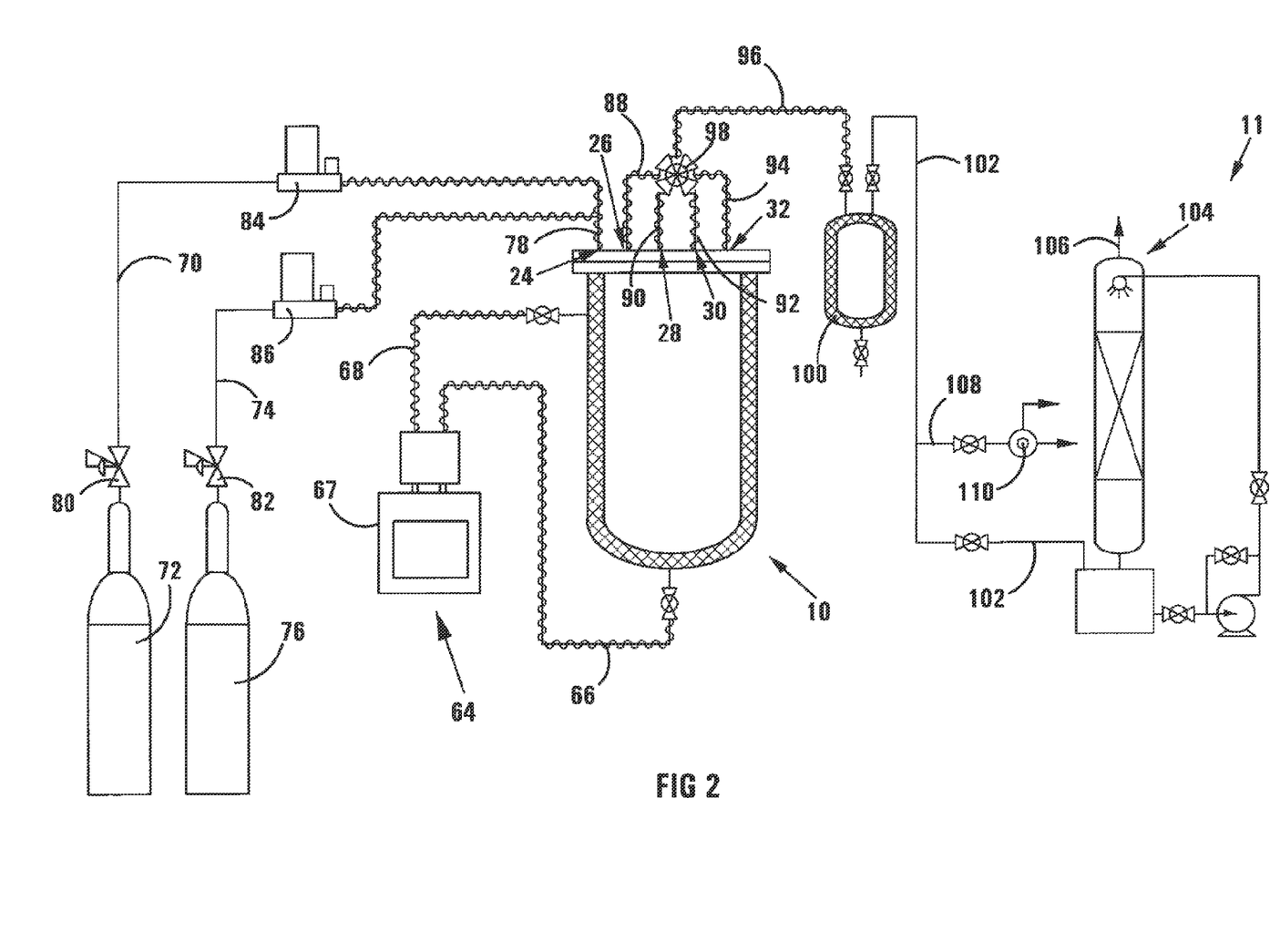
FIG. 2 shows, in simplified block diagram form, a process, according to the invention, for producing HFPO implemented by a pilot plant.

Referring to FIGS. 1 and 2, reference numeral 10 indicates a reactor in which a process for producing HFPO in accordance with the invention can be carried out. FIG. 2 shows a pilot plant 11 for implementing the process. The reactor 10 comprises a bank of four helical reactor coils 12a, 12b, 12c, 12d and a jacket 14, the reactor coils 12a, 12b, 12c, 12d being located within the jacket 14. The jacket 14 includes a cylindrical wall 16 with a radially outwardly projecting flange 17 at an upper end thereof. The jacket 14 includes a lower dished end 18 which is welded to the wall 16 and a circular top 20 which is secured to the flange 17 by means of six circumferentially spaced M22 bolts 22. FIG. 1 shows the reactor 10 in an open condition, with the top 20 spaced above the flange 17. However, in use, the reactor 10 is closed, with the top 20 adjacent the flange 17, the jacket 14 being sealed. Each reactor coil 12a, 12b, 12c, 12d has a surface-to-volume ratio of 2670 $m^{-1}$. The reactor coils 12 are immersed in a heat transfer fluid, in this example oil, contained within the jacket 14.

The reactor coils 12a, 12b, 12c, 12d were fabricated from ⅛ inch nominal size, copper refrigeration tubing and were formed from straight lengths of the tubing, which were bent into a coil shape and joined end-to-end to form the helical coils. Standard compression unions were used to join the individual lengths of tubing. The jacket 14 was fabricated from a length of 6-inch, schedule 40 304L stainless steel pipe 16. The flange 17 was drilled and tapped for receipt of the bolts 22.

The reactor has an inlet 24 and four outlets 26, 28, 30, 32. The inlet 24 and the outlets 26, 28, 30, 32 extend through the top 20. A flow line 34 leads into the reactor coil 12a and a flow line 36 leads from the reactor coil 12a. A connector 38 is located on flow line 36 and connects the flow line 36 to the outlet 26 and to a flow line 42. Flow line 42 leads to the reactor coil 12b, and a flow line 44 leads from the reactor coil 12b. A connector 46 is located on flow line 44 and connects the flow line 44 to the outlet 28 and to a flow line 50. Flow line 50 leads to the reactor coil 12c, and a flow line 52 leads from the reactor coil 12c. A connector 54 is located on the flow line 52 and connects the flow line 52 to the outlet 30 and to a flow line 58. Flow line 58 leads to the reactor coil 12d, and a flow line 60 leads from the reactor coil 12d to the outlet 32. The aggregate volume of the reactor coils 12a, 12b, 12c, 12d is $2.65 \times 10^{-4}$ m$^3$, and the aggregate length of the reactor coils 12a, 12b, 12c, 12d is 150 m.

An external oil-bath heating and circulating apparatus 64 (FIG. 2) is used to raise and maintain the temperature of the reactor coils 12a, 12b, 12c, 12d, line 66 leading from an oil reservoir 67 to the reactor 10 and line 68 leading from the reactor 10 to the reservoir 67. To monitor the reaction temperature, type K thermocouples (not shown) were inserted into the reactor tube at a position 200 mm from the inlet 24 and 200 mm from each of the outlets 26, 28, 30, 32, as well as midway along the length of each reactor coil 12a, 12b, 12c, 12d.

The pilot plant 11 includes a flow line 70 which leads from a gaseous HFP source 72 and includes a flow line 74 which leads from an oxygen source 76. The flow lines 70, 74 lead to a very short common flow line 78 (essentially an asymmetric T connector). The flow line 78 leads to the inlet 24 of the reactor 10. To control the flow rate of HFP, forward pressure regulator 80 and thermal mass flow controller 84 are provided on the flow line 70. To control the flow rate of oxygen, forward pressure regulator 82 and thermal mass flow controller 86 are provided on the flow line 74.

Flow lines 88, 90, 92, 94 respectively lead from the reactor outlets 26, 28, 30, 32 to a common flow line 96 via a 5-port, 4-way switching valve 98. By means of the switching valve 98, one or more of the flow lines 88, 90, 92, 94 can selectively be closed off. In this way, the length of the reaction zone in the reactor 10 can be varied. The flow line 96 leads to a catch pot 100. A flow line 102 leads from the catch pot 100 to an off-gas KOH scrubber 104, which has an outlet 106 at a top thereof for venting off the scrubbed gaseous product. The scrubber 104 is equipped with 20 mm nylon Pall rings and is charged with a 20wt % aqueous solution of potassium hydroxide. A sample line 108 leads off from the line 102 to an automated, pneumatically-driven 6-port sample valve 110 equipped with a 300 μl sample loop. The valve 110 is connected to two gas chromatographs (not shown) and to a wet test meter (not shown). The flow lines 78, 88, 90, 92, 94, 96 and the portions of the flow lines 70 and 74 that respectively lead from the mass flow controllers 84, 86 to the flow line 78 are heat traced lines, the temperature of these lines being maintained between 60° C. and 100° C., preferably 80° C.

Various trials of the process for producing HFPO were conducted, the reactor 10 being operated, after pretreatment of the reactor coils, at various reaction temperatures, gaseous residence times (space times) and HFP/O$_2$ molar feed ratios. In particular, various reaction temperatures selected within a range of 180 to 230° C., various space times in the reaction zones were selected within a range of 80 to 160 seconds and various HFP/O$_2$ molar feed ratios were selected within a range of 0.25:1 and 1.81:1. Only a single factor (i.e. reaction temperature, space time or HFP/O$_2$ molar feed ratios) was varied at a time, whilst maintaining the other two factors at fixed values.

To pretreat the reactor 10, the reactor coils are heated to a selected pretreatment temperature ($T_p$) for the epoxidation process, and thereafter gaseous HFP and oxygen is passed through the reactor 10 while maintaining the pretreatment temperature, the molar feed ratio of the HFP and the oxygen being approximately 1:1, the flow rate of the HFP/O$_2$ fed to the reactor 10 being 100-200 ml/min and the average total pressure in the reactor 10 being 4.5 bar. The conversion of HFP and yield of HFPO was found to stabilize after approximately 80 hours, at higher yield values than those obtained for the original newly installed reactor tube before the pretreatment. The operating temperature is maintained by means of the oil-bath heating and circulating apparatus 64. It has been found that pretreatment need only be performed once for newly installed reactor coils. After the pretreatment, if subsequent conversion of HFP by means of epoxidation to HFPO is stopped at some time and then restarted, then another pretreatment is not necessary.

To conduct each trial after the pretreatment of the reactor coils, the HFP:O$_2$ molar feed ratio was adjusted to the HFP:O$_2$ molar feed ratio selected for the trial, while still maintaining the reaction temperature ($T_r$), the HFP and oxygen being continuously fed into one end of the reactor 10 via the inlet 24 and the reaction products being withdrawn continuously from the exit end via the outlet 26 or 28 or 30 or 32. In particular, the length of the reaction zone and thus the gaseous residence time (space time) in the reactor 10 was selected by using the switching valve 98 to selectively close off one or more of the flow lines 88, 90, 92, 94 (thereby adjusting the effective length of the reaction zone) and making an appropriate adjustment of the total inlet flow rate of the reactants. In this way, various space times in the reaction zones were selected within a range of 80 to 160 seconds.

The flow rates of the HFP and the oxygen were controlled using the mass-flow controllers 84, 86. The HFP feed gas was found to be 99.8% pure via gas-chromatography, with HFPO and trace amounts of hexafluorocyclopropane as impurities. Oxidation in the reaction zone was implemented under isothermal conditions, the temperature being maintained by means of the oil-bath heating and circulating apparatus 64 at a temperature selected by a thermostat (not shown), and at an average total pressure of 4.5 bar. The pressure drop over the reactor zone was less than 10% of the total operating pressure. The product from the reactor 10 was scrubbed through the off-gas scrubber 104 to remove noxious gases prior to venting via the outlet 106, the product being contacted with the KOH solution in a counter-current fashion. It will be appreciated that in a commercial implementation to the process (not shown), a portion of the product from the reactor may be recycled through the reactor, and the portion of the product that is not recycled may be sent to a separation stage to separate out the HFPO from remainder of the reactor effluent.

During the production process, samples of the product gas were withdrawn via flow line 108 for composition analysis. Samples were withdrawn from the reactor exit stream via the valve 110. The analyses of gaseous products were performed using two gas chromatographs (not shown) which were operated with an injection split ratio of 175:1. The mole fractions of HFPO, HFP, hexafluorocyclopropane (cyclo-$C_3F_6$) and tetrafluoroethylene ($C_2F_4$) were established using a Shimadzu G.C. 2010 gas chromatograph equipped with an Agilent GS-GasPro PLOT column (30 m×0.32 mm ID) as well as both a thermal conductivity detector and a flame ionization detector. The column oven was operated isothermally at 30° C. for 25 minutes. Unreacted oxygen and the acid fluoride byproducts, i.e. carbonyl fluoride ($COF_2$) and trifluoroacetyl fluoride ($CF_3COF$), were separated on a Shimadzu G.C. 2014 gas chromatograph equipped with a Hayesep D packed column and a thermal conductivity detector. This analysis was carried out isothermally at 95° C.

The performance of the coiled laminar-flow reactor 10 (with a very high length-to-diameter ratio of 76200) was well approximated by a simply plug flow reactor model, as a result of the flattening of the radial concentration profiles through extensive radial diffusion and secondary flow through the action of centrifugal force on fluid elements.

Figure 3:
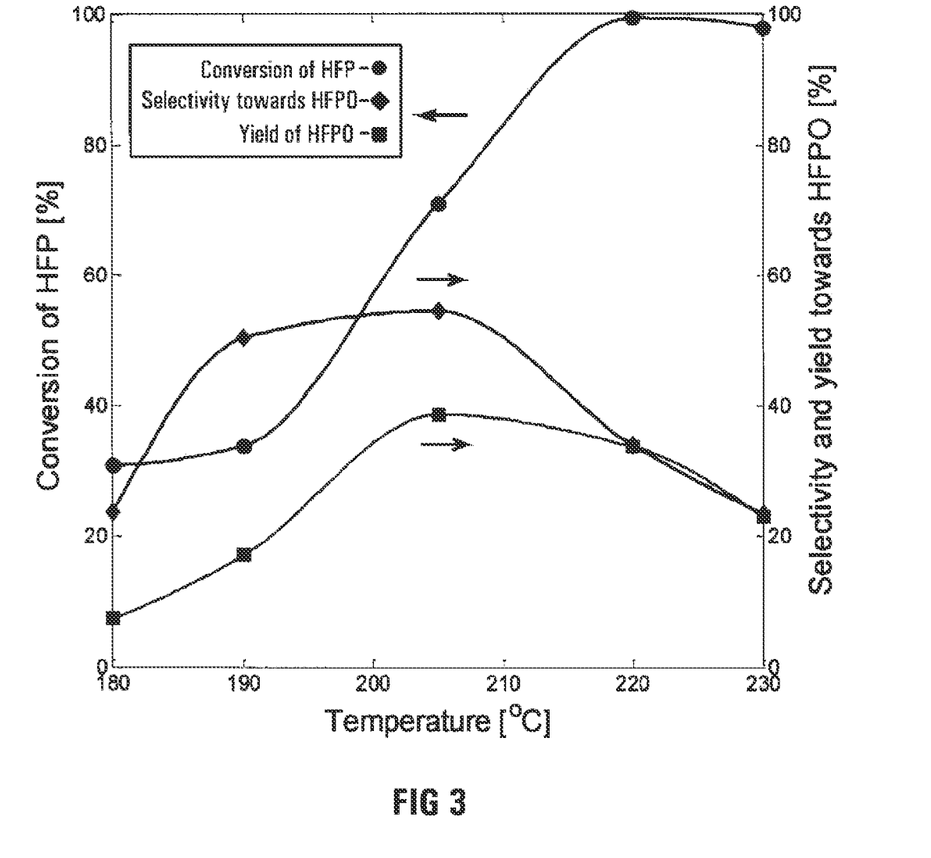
FIG. 3 is a plot showing the effect of reaction temperature on the conversion of HFP, selectivity towards HFPO and yield of HFPO, at a fixed HFP/$O_2$ molar feed ratio (1 mol/mol) and space time (120 seconds)
Figure 4:
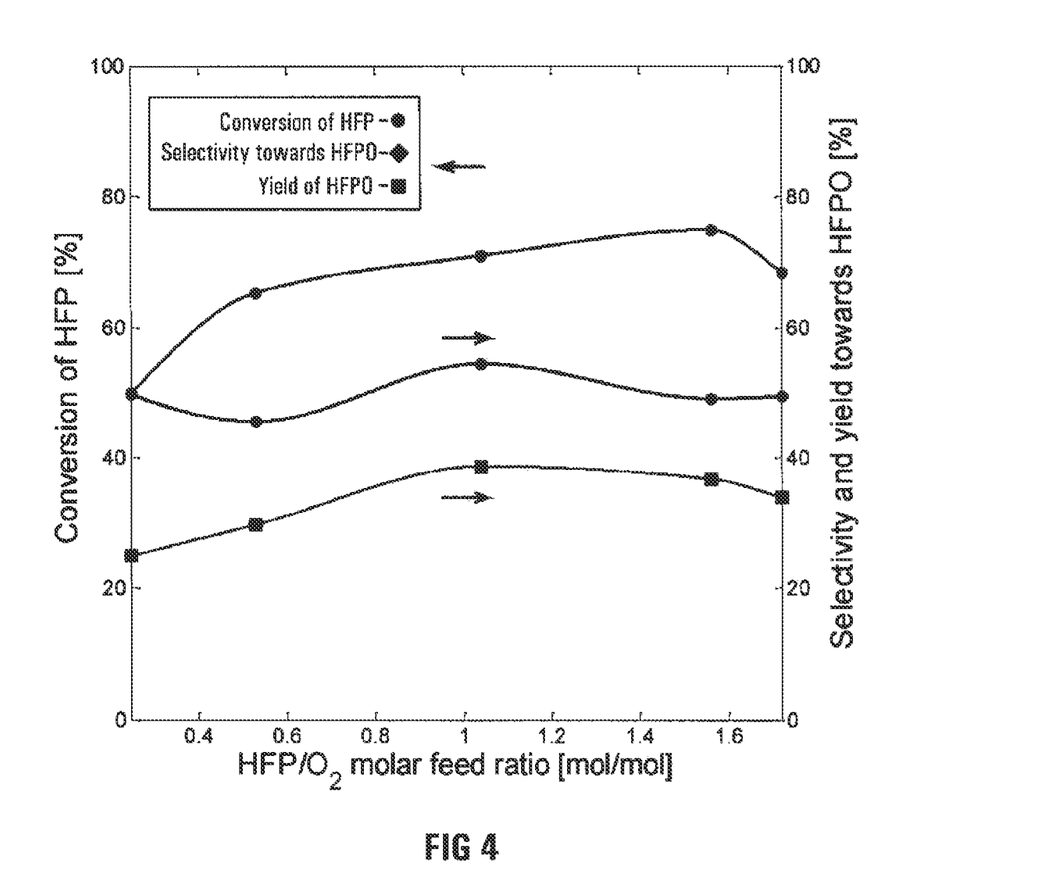
FIG. 4 is a plot showing the effect of HFP/$O_2$ molar feed ratio on the conversion of HFP, selectivity towards HFPO and yield of HFPO, at a fixed reaction temperature (205° C.) and space time (120 seconds)
Figure 5:
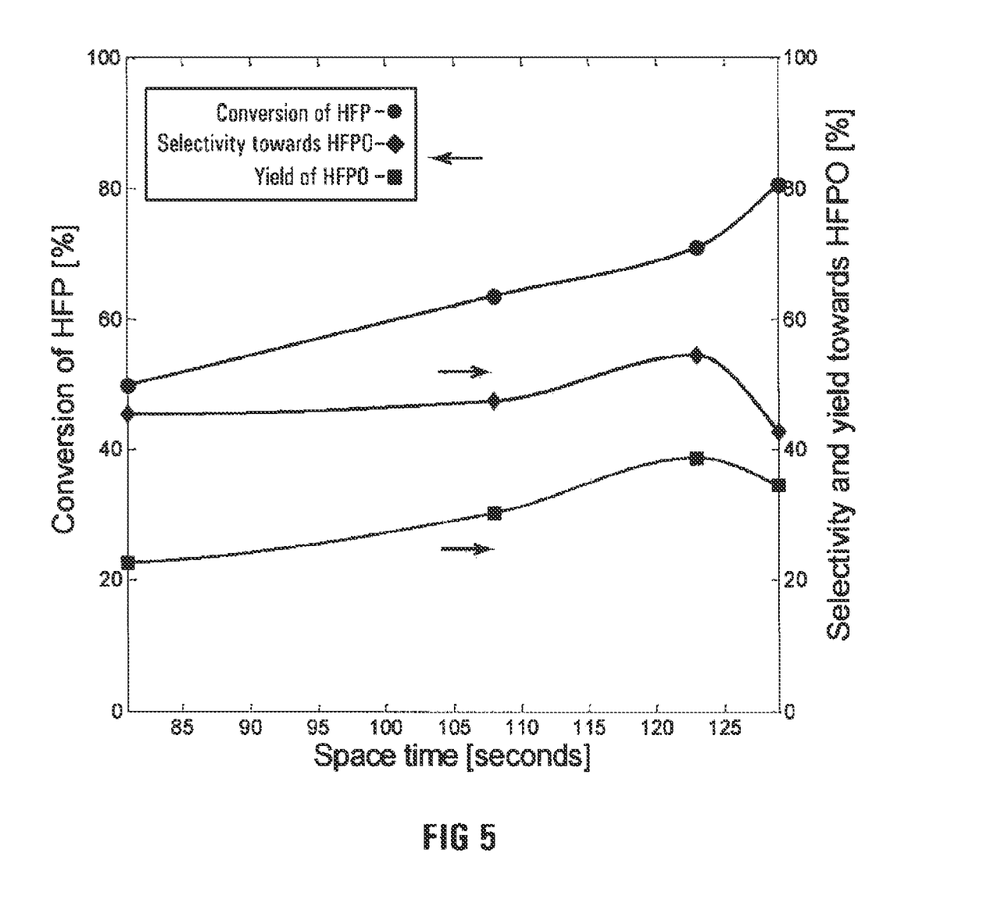
FIG. 5 is a plot showing the effect of space time on the conversion of HFP, selectivity towards HFPO and yield of HFPO, at a fixed reaction temperature (205° C.) and HFP/$O_2$ molar feed ratio (1 mol/mol)

FIGS. 2 to 4 show the effect of three operating variables (reaction temperature, molar feed ratio and space time) on the conversion of HFP, selectivity towards HFPO and yield of HFPO. For the purposes of this specification, conversion of HFP, selectivity towards HFPO and yield of HFPO, are defined by the following equations respectively:

$$X_{HFP} = \frac{F^0_{HFP} - F_{HFP}}{F^0_{HFP}} \times 100\% \quad (1)$$

$$S_{HFPO} = \frac{F_{HFPO}}{F^0_{HFP} - F_{HFP}} \times 100\% \quad (2)$$

$$Y_{HFPO} = \frac{F_{HFPO}}{F^0_{HFP}} \times 100\% \quad (3)$$

where:
$F_i$=outlet molar flow rate of component i, mol s$^{-1}$
$F_i^0$=inlet molar flow rate of component i, mol s$^{-1}$
$X_{HFP}$=conversion of HFP, %
$S_{HFPO}$=selectivity towards HFPO, %
$Y_{HFPO}$=yield of HFPO, %

Figure 6:
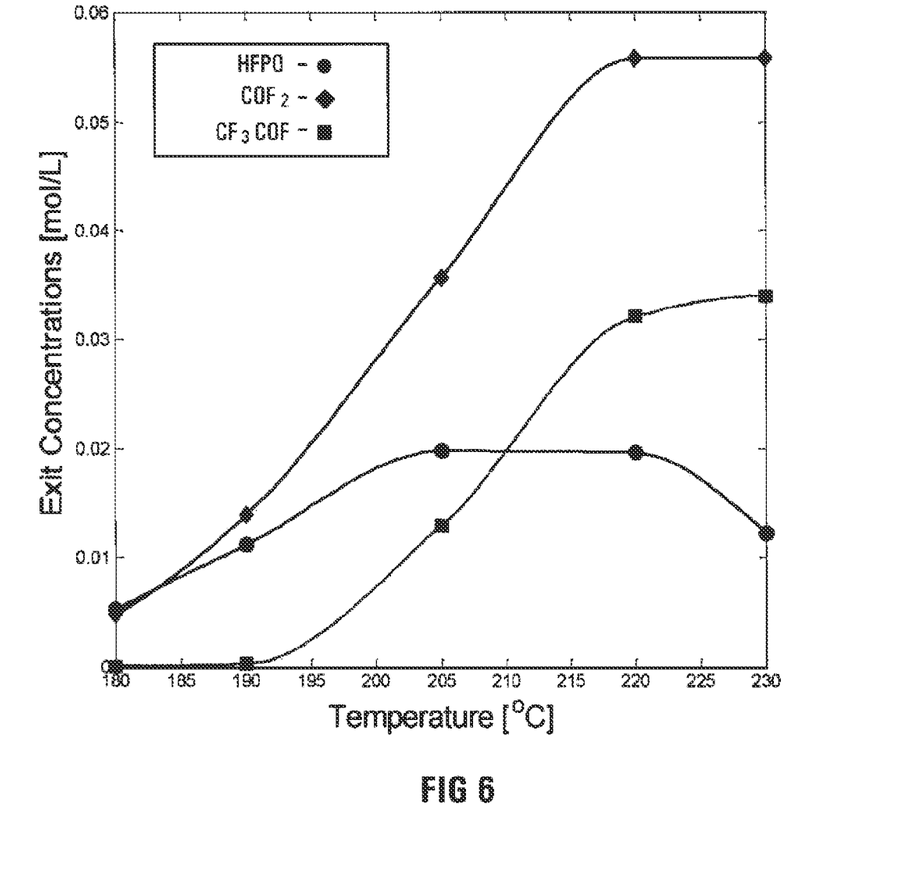
FIG. 6 is a plot showing the effect of reactor temperature on the concentration of HFPO, $COF_2$ and $CH_3COF$ in the product which exits the reactor, at a fixed HFP/$O_2$ molar feed ratio (1 mol/mol) and space time (120 seconds)
Figure 7:
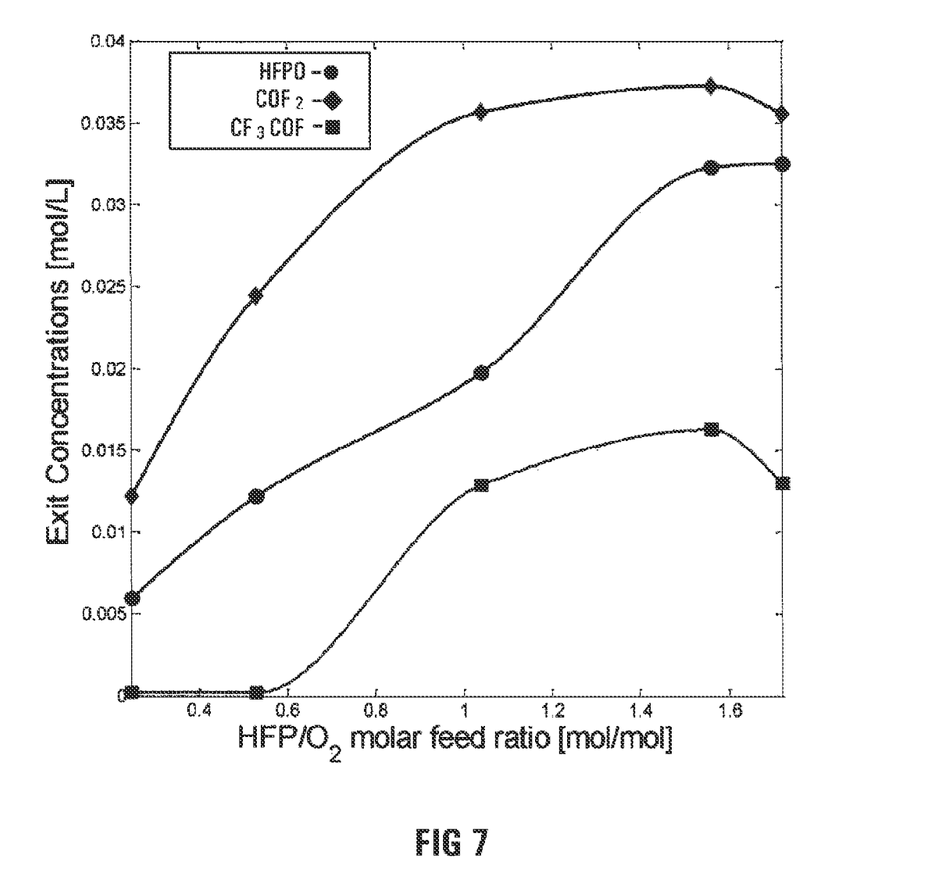
FIG. 7 is a plot showing the effect of HFP/$O_2$ molar feed ratio on the concentration of HFPO, $COF_2$ and $CH_3COF$ in the product which exits the reactor, at a fixed reaction temperature (205° C.) and space time (120 seconds)
Figure 8:
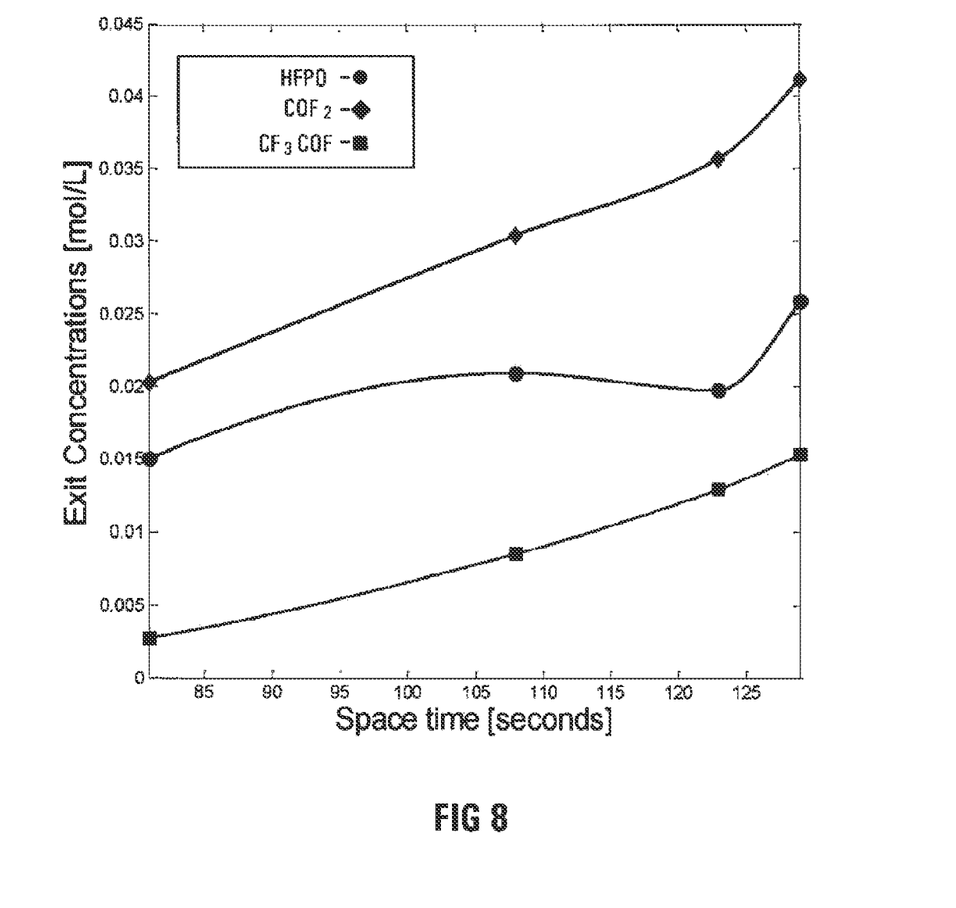
FIG. 8 is a plot showing the effect of space time on the concentration of HFPO, $COF_2$ and $CH_3COF$ in the product which exits the reactor, at a fixed reaction temperature (205° C.) and HFP/$O_2$ molar feed ratio (1 mol/mol)

FIGS. 6 to 8 respectively show the effect of reaction temperature, HFP/$O_2$ molar feed ratio and space time on the concentration HFPO, $COF_2$ and $CF_3COF$ in the product which exits the reactor 10.

In order to further assess the effect of operating conditions on the product distribution obtained from the gas-phase oxidation of HFP and to probe for optimal reaction conditions, a central composite experimental design was used, reaction temperature ($X_1$), HFP/$O_2$ molar feed ratio ($X_2$) and space time ($X_3$) being chosen as the variables to be considered. The central composite design consisted of 20 experiments composed of a two-level, full-factorial design, 4 axial design points and 6 centre points.

The selected test limits for each variable are presented in Table 1, along with the observed responses.

The relationship between the independent variables and the response function (either HFPO selectivity or HFPO yield) was approximated by a quadratic response surface model, which in general form is given by Equation 4, $$Y = \beta_0 + \sum_{i=1}^{3} \beta_i X_i + \sum_{i=1}^{3} \beta_{ii} X_i^2 + \sum_{i<j} \sum_{j} \beta_{ij} X_i X_j \quad (4)$$

where Y is the predicted response, $\beta_0$ is the intercept coefficient, $\beta_i$ are the coefficients of the linear terms, $\beta_{ii}$ are the coefficients of the squared terms, $\beta_{ij}$ are the coefficients of the interaction terms and $X_i$ and $X_j$ are the independent variables. The coefficients of the full quadratic polynomial expression were established using the method of least squares to obtain Equations 5 and 6 below.

$$Y_{HFPO} = -2169.0252 + 17.9302 X_1 + 28.6987 X_2 + 5.1114 X_3 + 1.006 \times 10^{-1} X_1 X_2 - 1.2640 \times 10^{-2} X_1 X_3 - 9.9461 \times 10^{-2} X_2 X_3 - 3.9314 \times 10^{-2} X_1^2 - 16.3222 X_2^2 - 9.6724 \times 10^{-3} X_3^2 \quad (5)$$

$$S_{HFPO} = -2486.2318 + 22.0926 X_1 + 18.3312 X_2 + 4.6853 X_3 + 2.3359 \times 10^{-1} X_1 X_2 - 9.2480 \times 10^{-3} X_1 X_3 - 3.1757 \times 10^{-1} X_2 X_3 - 5.2091 \times 10^{-2} X_1^2 - 11.3147 X_2^2 - 1.0443 \times 10^{-2} X_3^2 \quad (6)$$

Figure 9:
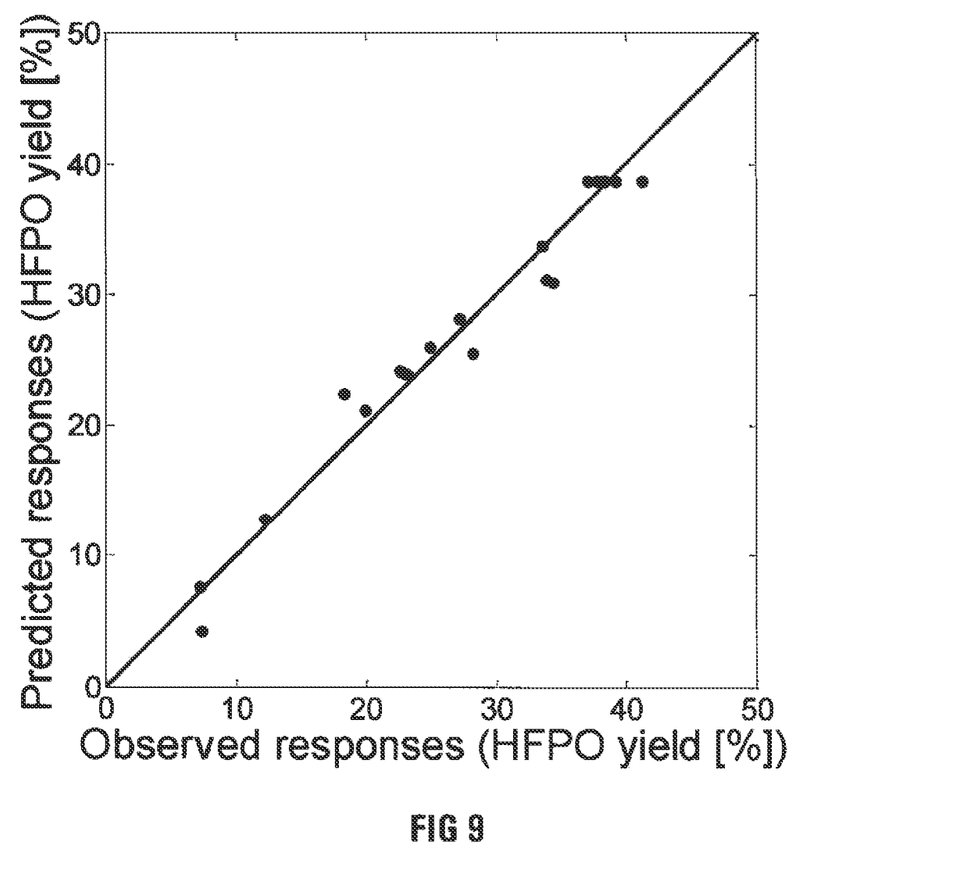
FIG. 9 is a parity plot showing the observed HFPO yield and the HFPO yield predicted by a quadratic response surface model.
Figure 10:
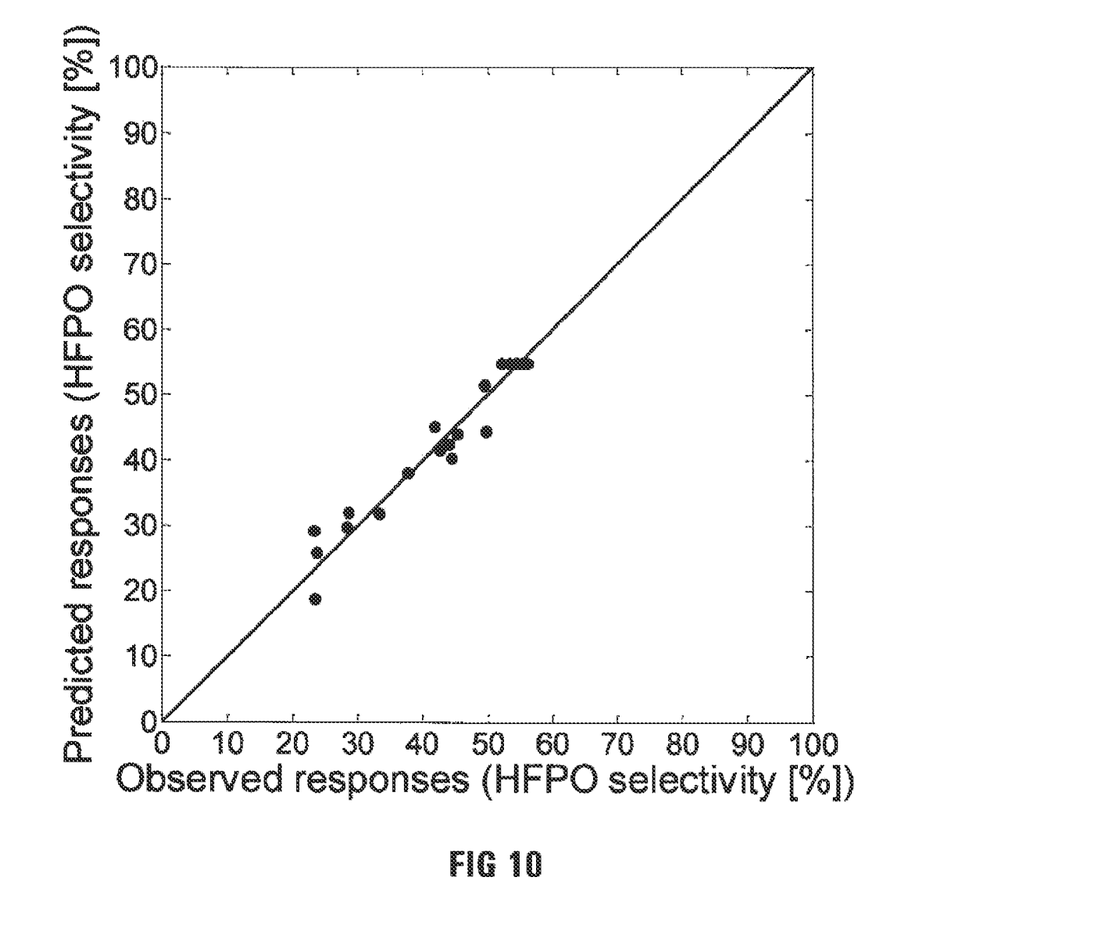
FIG. 10 is a parity plot showing the observed HFPO selectivity and the HFPO selectivity predicted by a quadratic response surface model.

The adequacy of each model was checked and confirmed with an analysis of variance (ANOVA) test. The results are presented in Table 2. Parity plots of the observed and predicted responses, i.e. HFPO yield and HFPO selectivity, are presented in FIGS. 9 and 10, respectively. The coefficients of multiple determination for each model were found to be satisfactory. The computed value of the Fischer test statistic was greater than the tabulated value $F_{(p-1, N-p, \alpha)}$ (p is the number of parameters in the model, N is the number of experiments and $\alpha$ in this case represents the significance level) of 4.94 at the 99% level of significance, for both models, indicating a statistically significant regression. The least squares regression results and significance effects of the regression coefficients for the HFPO yield and HFPO selectivity models are presented in Tables 3 and 4, respectively.

TABLE 1

Central composite design and experimental

| Run[a] | $X_1$ Temperature [° C.] | Level[b] | $X_2$ HFP/$O_z$ Feed ratio [mol/mol] | Level[b] | $X_3$ Space time [seconds] | Level[b] | Conversion of HFP [%] | HFPO selectivity [%] | HFPO Yield [%] |
|---|---|---|---|---|---|---|---|---|---|
| F1 | 190 | −1 | 0.5 | −1 | 100 | −1 | 25.22 | 28.55 | 7.20 |
| F2 | 220 | +1 | 0.5 | −1 | 100 | −1 | 99.51 | 28.30 | 28.17 |
| F3 | 190 | −1 | 1.5 | +1 | 100 | −1 | 27.36 | 44.47 | 12.16 |
| F4 | 220 | +1 | 1.5 | +1 | 100 | −1 | 80.33 | 41.75 | 33.54 |
| F5 | 190 | −1 | 0.5 | −1 | 140 | +1 | 45.33 | 43.96 | 19.93 |
| F6 | 220 | +1 | 0.5 | −1 | 140 | +1 | 99.90 | 23.14 | 23.11 |
| F7 | 220 | +1 | 1.5 | +1 | 140 | +1 | 81.30 | 33.36 | 27.12 |
| F8 | 190 | −1 | 1.5 | +1 | 140 | +1 | 48.55 | 37.70 | 18.30 |

TABLE 1-continued

Central composite design and experimental

| Run[a] | $X_1$ Temperature [°C.] | Level[b] | $X_2$ HFP/$O_2$ Feed ratio [mol/mol] | Level[b] | $X_3$ Space time [seconds] | Level[b] | Conversion of HFP [%] | HFPO selectivity [%] | HFPO Yield [%] |
|---|---|---|---|---|---|---|---|---|---|
| S1 | 205 | 0 | 1 | 0 | 86 | −α | 71.63 | 53.43 | 38.28 |
| S2 | 205 | 0 | 1 | 0 | 154 | +α | 49.86 | 45.33 | 22.60 |
| S3 | 205 | 0 | 0.25 | −α | 120 | 0 | 80.59 | 42.63 | 34.36 |
| S4 | 205 | 0 | 1.841 | +α | 120 | 0 | 49.99 | 49.86 | 24.93 |
| S5 | 180 | −α | 1 | 0 | 120 | 0 | 68.45 | 49.57 | 33.93 |
| S6 | 230 | +α | 1 | 0 | 120 | 0 | 30.92 | 23.69 | 7.33 |
| C1 | 205 | 0 | 1 | 0 | 120 | 0 | 97.98 | 23.40 | 22.93 |
| C2 | 205 | 0 | 1 | 0 | 120 | 0 | 70.94 | 52.24 | 37.06 |
| C3 | 205 | 0 | 1 | 0 | 120 | 0 | 74.52 | 55.38 | 41.27 |
| C4 | 205 | 0 | 1 | 0 | 120 | 0 | 70.47 | 54.45 | 38.37 |
| C5 | 205 | 0 | 1 | 0 | 120 | 0 | 70.67 | 55.51 | 39.23 |
| C6 | 205 | 0 | 1 | 0 | 120 | 0 | 67.31 | 56.17 | 37.81 |

[a]F = orthogonal factorial design points, S = axial design points, C = centre points
[b]−1 = low value, 0 = centre point value, +1 = high value, −α = low axial value, +α = high axial value

TABLE 2

ANOVA results and regression statistics for the HFPO yield and selectivity response models

| Statistics | HFPO yield model | HFPO selectivity model |
|---|---|---|
| $R^2$ | 0.966 | 0.9389 |
| Adjusted $R^2$ | 0.936 | 0.884 |
| Standard error | 2.680 | 3.980 |
| F-statistic | 32.144 | 17.073 |
| p-value | $3.223 \times 10^{-6}$ | $6.064 \times 10^{-5}$ |
| Regression Mean Square | 231.016 | 270.336 |
| Residual Mean Square | 7.186 | 15.834 |

TABLE 3

Least squares regression results and significance effects of the regression coefficients for the HFPO yield model.

| Parameter | Term | Coefficient | t-value | p-value |
|---|---|---|---|---|
| $\beta_0$ | intercept | −2169.0252 | −13.4617 | $9.8432 \times 10^{-8}$ |
| $\beta_1$ | $X_1$ | 17.9302 | 13.1465 | $1.2330 \times 10^{-7}$ |
| $\beta_2$ | $X_2$ | 28.6987 | 0.9890 | $3.4599 \times 10^{-1}$ |
| $\beta_3$ | $X_3$ | 5.1114 | 6.5857 | $6.1877 \times 10^{-5}$ |
| $\beta_{12}$ | $X_1 X_2$ | $1.006 \times 10^{-1}$ | 0.7960 | $4.4451 \times 10^{-1}$ |
| $\beta_{13}$ | $X_1 X_3$ | $-1.2640 \times 10^{-2}$ | −4.0009 | $2.5146 \times 10^{-3}$ |
| $\beta_{23}$ | $X_2 X_3$ | $-9.9461 \times 10^{-2}$ | −1.0493 | $3.1870 \times 10^{-1}$ |
| $\beta_{11}$ | $X_1^2$ | $-3.9314 \times 10^{-2}$ | −12.3696 | $2.1953 \times 10^{-7}$ |
| $\beta_{22}$ | $X_2^2$ | −16.3222 | −5.3302 | $3.3284 \times 10^{-4}$ |
| $\beta_{33}$ | $X_3^2$ | $-9.6724 \times 10^{-2}$ | −5.5872 | $2.3176 \times 10^{-4}$ |

TABLE 4

Least squares regression results and significance effects of the regression coefficients for the HFPO selectivity model.

| Parameter | Term | Coefficient | t-value | p-value |
|---|---|---|---|---|
| $\beta_0$ | intercept | −2486.2318 | −10.3955 | $1.1127 \times 10^{-6}$ |
| $\beta_1$ | $X_1$ | 22.0926 | 10.9129 | $7.0974 \times 10^{-7}$ |
| $\beta_2$ | $X_2$ | 18.3312 | 0.4255 | $6.7942 \times 10^{-1}$ |
| $\beta_3$ | $X_3$ | 4.6853 | 4.0669 | $2.2612 \times 10^{-3}$ |
| $\beta_{12}$ | $X_1 X_2$ | $2.3359 \times 10^{-1}$ | 1.2452 | $2.4142 \times 10^{-1}$ |
| $\beta_{13}$ | $X_1 X_3$ | $-9.2480 \times 10^{-3}$ | −1.9720 | $7.6882 \times 10^{-2}$ |
| $\beta_{23}$ | $X_2 X_3$ | $-3.1757 \times 10^{-1}$ | −2.2572 | $4.7587 \times 10^{-2}$ |
| $\beta_{11}$ | $X_1^2$ | $-5.2091 \times 10^{-2}$ | −11.0417 | $6.3645 \times 10^{-7}$ |
| $\beta_{22}$ | $X_2^2$ | −11.3147 | −2.4891 | $3.2035 \times 10^{-2}$ |
| $\beta_{33}$ | $X_3^2$ | $-1.0443 \times 10^{-2}$ | −4.0641 | $2.2713 \times 10^{-3}$ |

Interaction surface and contour plots for each combination of operating variables were generated using the two quadratic response models (Equations 5 and 6 above) and, with the use of a Nelder-Mead simplex optimization algorithm, optimum operating points for HFPO yield and HFPO selectivity were obtained. In particular, an optimum HFPO yield of 40% was obtained at 210° C., using a HFP/$O_2$ molar feed ratio of 1.158 and a space time of 120 seconds. An optimum HFPO selectivity of 56% was obtained at 205° C., using a HFP/$O_2$ molar feed ratio of 1.337 and a space time of 113 seconds. A combined optimum HFPO yield of 39.5% and HFPO selectivity of 55.2% (i.e. best trade-off between HFPO selectivity and HFPO yield) was obtained at 207° C., with a HFP/$O_2$ molar feed ratio of 1.210 and a space time of 118 seconds.

By means of the invention, a process is provided which can achieve a relatively high rate of production of HFPO, without the use of a catalyst and which avoids the use of large quantities of solvents and/or chemical oxidising agents such as hypohalites, hydrogen peroxide and organic peroxides. The process, as illustrated and described above, is relatively simple and is conducted at a relatively low pressure 4.5 bar as compared with some conventional processes, thus reducing the possibility of detonation.

The invention claimed is:

1. A process for the production of hexafluoropropylene oxide, which process includes:
pretreating a reactor by heating a reaction zone of the reactor to a pretreatment temperature $T_p$, where 180° C.$\leq T_p \leq$230° C., and thereafter passing a feedstock comprising gaseous hexafluoropropylene and molecular oxygen through the heated reaction zone at a first hexafluoropropylene:$O_2$ molar ratio, x, which is about 1:1, for a period of time, while maintaining the pretreatment temperature $T_p$ in the reaction zone;
thereafter adjusting the hexafluoropropylene:$O_2$ molar ratio to a second value, y, which is in the range of 0.25:1 to 1.81:1, and where y≠x, with the reaction zone being at a reaction temperature $T_r$, where 180° C.$\leq T_r \leq$230° C.;
allowing the feedstock to react, by epoxidation of the hexafluoropropylene, to produce hexafluoropropylene oxide; and
withdrawing the hexafluoropropylene oxide from the reaction zone, with the introduction of the feedstock into the reaction zone and the withdrawal of the product from the reaction zone being continuous.

2. The process of claim 1, wherein the reactor comprises a copper-based cylindrical tube of constant cross-sectional area, with the tube being helically coiled and having a surface-to-volume ratio >2000m$^{-1}$ such that there is laminar flow of the feedstock and the hexafluoropropylene oxide through the reaction zone.

3. The process according to claim 1, wherein the pretreatment temperature, $T_p$, is approximately 200° C.

4. The process according to claim 1, wherein the molar ratio, y, of hexafluoropropylene:$O_2$ is in the range of 1.1:1 to 1.35:1.

5. The process according to claim 1, wherein the period of time that the reactor is pretreated is at least 60 hours.

6. The process according to claim 1, wherein the pressure in the reactor, during the pretreatment as well as subsequently, is 3 to 6.5 bar.

7. The process according to claim 1, wherein the gaseous residence time of the feedstock in the reaction zone during the pretreatment as well as subsequently, during the hexafluoropropylene conversion to hexafluoropropylene oxide, is in the range of 80 to 160 seconds.

8. A process for the production of hexafluoropropylene oxide, which includes pretreating a reactor by heating a reaction zone of the reactor to a pretreatment temperature $T_p$, where 180° C. $\leq T_p \leq$ 230° C., and thereafter passing gaseous hexafluoropropylene and oxygen through the reaction zone at a first hexafluoropropylene:$O_2$ molar ratio, x, of about 1:1, for a period of time, while maintaining the pretreatment temperature $T_p$ in the reaction zone; and thereafter adjusting the hexafluoropropylene:$O_2$ molar ratio to a second value, y, which is in the range of 0.25:1 to 1.81:1, and where y $\neq$ x, with the hexafluoropropylene being converted by means of epoxidation to hexafluoropropvlene oxide.

\* \* \* \* \*